US010265226B2

(12) United States Patent
Watanabe et al.

(10) Patent No.: US 10,265,226 B2
(45) Date of Patent: Apr. 23, 2019

(54) WATER-ABSORBENT RESIN, WATER-ABSORBENT MATERIAL, AND WATER-ABSORBENT ARTICLE

(71) Applicant: SUMITOMO SEIKA CHEMICALS CO., LTD., Kako-gun, Hyogo (JP)

(72) Inventors: Ayaka Watanabe, Saitama (JP); Kimihiko Kondo, Osaka (JP); Junichi Takatori, Himeji (JP)

(73) Assignee: Sumitomo Seika Chemicals Co., Ltd., Kako-Gun, Hyogo (JP)

( * ) Notice: Subject to any disclaimer, the term of this patent is extended or adjusted under 35 U.S.C. 154(b) by 390 days.

(21) Appl. No.: 14/426,940

(22) PCT Filed: Aug. 1, 2013

(86) PCT No.: PCT/JP2013/070919
§ 371 (c)(1),
(2) Date: Mar. 9, 2015

(87) PCT Pub. No.: WO2014/038324
PCT Pub. Date: Mar. 13, 2014

(65) Prior Publication Data
US 2015/0216740 A1  Aug. 6, 2015

(30) Foreign Application Priority Data
Sep. 10, 2012 (JP) ................. 2012-198832

(51) Int. Cl.
| C08F 20/06 | (2006.01) |
| A61F 13/53 | (2006.01) |
| A61F 13/49 | (2006.01) |
| A61L 15/60 | (2006.01) |
| C08F 2/32 | (2006.01) |
| C08J 3/24 | (2006.01) |
| C08F 122/02 | (2006.01) |
| C08L 33/02 | (2006.01) |
| C08F 2/14 | (2006.01) |
| C08F 2/18 | (2006.01) |
| C08J 3/075 | (2006.01) |
| B01J 20/26 | (2006.01) |

(52) U.S. Cl.
CPC .............. *A61F 13/53* (2013.01); *A61F 13/49* (2013.01); *A61L 15/60* (2013.01); *B01J 20/267* (2013.01); *C08F 2/14* (2013.01); *C08F 2/18* (2013.01); *C08F 2/32* (2013.01); *C08F 122/02* (2013.01); *C08J 3/075* (2013.01); *C08J 3/245* (2013.01); *C08L 33/02* (2013.01); *C08J 2333/02* (2013.01); *Y10T 428/31855* (2015.04)

(58) Field of Classification Search
CPC ...... C08F 2/32; C08F 2/14; C08F 2/18; C08L 33/02
See application file for complete search history.

(56) References Cited

U.S. PATENT DOCUMENTS

2008/0280154 A1* 11/2008 Kobushi ................. A61L 15/60
428/500
2013/0018349 A1   1/2013 Takatori et al.

FOREIGN PATENT DOCUMENTS

| EP | 0 317 106 B1 | 2/1993 |
| EP | 0 349 241 B1 | 8/1996 |
| EP | 0 349 240 B1 | 4/1997 |
| EP | 0 761 241 B1 | 6/2003 |
| EP | 1 609 810 A1 | 12/2005 |
| EP | 1 714 985 A1 | 10/2006 |
| EP | 1 900 755 A1 | 3/2008 |
| EP | 2 184 300 A1 | 5/2010 |
| EP | 2 011 803 B1 | 9/2011 |
| EP | 2 631 251 A1 | 8/2013 |
| EP | 2 700 659 A1 | 2/2014 |
| EP | 3 168 241 A1 | 5/2017 |
| JP | 63-092701 A | 4/1988 |
| JP | 2003-088552 A | 3/2003 |
| JP | 2003-206381 A | 7/2003 |
| JP | 2006-089525 A | 4/2006 |
| JP | 2012-001735 A | 1/2012 |
| TW | 201143738 A | 12/2011 |

(Continued)

OTHER PUBLICATIONS

Extended European Search Report in related European Application No. 13834858.6, dated Mar. 18, 2016.
Buchholz & Graham 1998 in *Modern superabsorbent polymer technology*, Fredric L. Buchholz and Andrew T. Graham, eds., pp. 149-153.
Notice of Opposition to a European Patent in related European Application No. EP13834858.6, dated Aug. 7, 2018.

(Continued)

*Primary Examiner* — Margaret G Moore
(74) *Attorney, Agent, or Firm* — Knobbe, Martens, Olson & Bear LLP

(57) ABSTRACT

One purpose of the present invention is to provide a water-absorbent resin having excellent water absorption characteristics and being capable of improving the shape-retaining characteristics of a water-absorbent material when used in the water-absorbent material. A water-absorbent resin obtained by performing reversed phase suspension polymerization of a water-soluble ethylenically unsaturated monomer in a hydrocarbon dispersion medium, using a radical polymerization initiator, said resin being capable of having both excellent absorption performance and shape retention in a water-absorbent material using the water-absorbent resin, as a result of fulfilling the conditions of: (1) having a water-retention capacity of physiological saline of at least 38 g/g; (2) having a water-absorption capacity of physiological saline under a load of 4.14 kPa of at least 15 ml/g; and (3) having a tan δ of a 50-fold swollen gel of at least $2.10 \times 10^{-2}$.

4 Claims, 1 Drawing Sheet

(56) References Cited

FOREIGN PATENT DOCUMENTS

| | | |
|---|---|---|
| WO | WO 2006/123561 A1 | 11/2006 |
| WO | WO 2012/053121 A1 | 4/2012 |
| WO | WO 2012/132902 A1 | 10/2012 |
| WO | WO 2012/176342 A1 | 12/2012 |
| WO | WO 2012/144566 A1 | 7/2014 |

OTHER PUBLICATIONS

Experimental Report of Reproduction of Example 3 of EP 0761241 B1, presented in Opposition, dated Aug. 7, 2018.
Experimental Report of Reproduction of Example 5 of EP 0317106 B1, presented in Opposition, dated Aug. 7, 2018.

* cited by examiner

WATER-ABSORBENT RESIN, WATER-ABSORBENT MATERIAL, AND WATER-ABSORBENT ARTICLE

TECHNICAL FIELD

The present invention relates to a water-absorbent resin and to an absorbent material and an absorbent article comprising the same. Particularly, the invention relates to a water-absorbent resin possessing excellent water-retention capacity of physiological saline, high water-absorption capacity of physiological saline under a load, and excellent viscoelasticity and to an absorbent material and an absorbent article comprising the same.

BACKGROUND ART

In recent years, water-absorbent resins have been widely used for various fields, including hygienic materials such as disposable diapers and sanitary napkins, agricultural and horticultural materials such as water retaining materials and soil conditioners, and industrial materials such as water-blocking agents and dew condensation prevention agents. Among these fields, the water-absorbent resins are most often used especially for hygienic materials such as disposable diapers and sanitary napkins.

As such water-absorbent resins, there are known, for example, hydrolysates of starch-acrylonitrile graft copolymers, neutralized products of starch-acrylic acid graft polymers, saponified products of vinyl acetate-acrylic acid ester copolymers, and crosslinked products of partially neutralized polymers of acrylic acid.

Incidentally, absorbent articles represented by disposable diapers, sanitary napkins and incontinence pads are composed of an absorbent material for absorbing and retaining a body liquid discharged from a human body, such as urine and menses, the material being disposed mainly at the central part, a liquid-permeable front sheet (top sheet) positioned on a side where the sheet comes into contact with a body and a liquid-impermeable rear sheet (back sheet) positioned on a side opposite from the side where the sheet comes into contact with the body. Usually, the absorbent material comprises hydrophilic fibers, such as pulp, and a water-absorbent resin.

The absorbent material temporally retains a liquid having entered through the front sheet with the hydrophilic fibers and then retains the liquid with the water-absorbent resin. Generally, to increase the liquid absorption amount of the absorbent material, it is effective to increase the amount of the water-absorbent resin and thereby relatively reduce the amount of the hydrophilic fibers. In the case of having increased the amount of the water-absorbent resin and thereby having reduced the amount of the hydrophilic fibers, however, there is a drawback that when the absorbent material has absorbed a liquid, the volume of the absorbent material increases due to swelling of the water-absorbent resin, causing decrease in intertwinement of the fibers themselves or of the water-absorbent resin with the fibers. Such decrease in intertwinement of the fibers themselves or of the water-absorbent resin with the fibers becomes a serious drawback in the case of using the water-absorbent material as a hygienic material because when compression or a shearing force is applied to the absorbent material, deformation such as cracking or uneven distribution occurs, and moreover inhibition of liquid absorption or re-wet of a liquid occurs.

As a method for preventing deformation of an absorbent material, there has heretofore been known a method of developing an adhesion force between thermally fused fibers or between pulp and thermally fused fibers by incorporating the thermally fused fibers into the pulp, and thereby improving the shape retention property of the absorbent material (see Patent Document 1). The method of Patent Document 1, however, has a problem that the liquid permeation rate and the absorption amount lower because the thermally fused fibers are hydrophobic though the shape retention property of an absorbent material is improved.

Against this background, it has been desired to develop a water-absorbent resin capable of improving the shape retention property of an absorbent material when being used for the absorbent material.

PRIOR ART DOCUMENT

Patent Document

Patent Document 1: Japanese Patent Laid-open Publication No. 63-92701

SUMMARY OF THE INVENTION

Problems to be Solved by the Invention

It is an object of the present invention to provide a water-absorbent resin being excellent in water absorption capacity and capable of improving the shape retention property of an absorbent material when having been used for the absorbent material. Another object of the present invention is to provide an absorbent material and an absorbent article utilizing the water-absorbent resin.

Means for Solving the Problem

As a result of earnest studies for solving the above-mentioned problems, the present inventors have found that it is possible to suppress deformation of an absorbent material comprising a water-absorbent resin and also possible to obtain an absorbent material not only being high in liquid permeation rate and capable of suppressing re-wet of a liquid having been absorbed, but also possessing both excellent absorption performance and excellent shape retention property, by making a water-absorbent resin obtained by performing reversed phase suspension polymerization of a water-soluble ethylenically unsaturated monomer using a radical polymerization initiator in a hydrocarbon dispersion medium fulfil specific ranges of water-retention capacity of physiological saline, water-absorption capacity of physiological saline under a load of 4.14 kPa, and tan δ of a 50-fold swollen gel. The present invention has been accomplished as a result of further studies based on such findings.

The present invention provides a water-absorbent resin, an absorbent material, and an absorbent article of the embodiments given below.

Item 1. A water-absorbent resin obtained by performing reversed phase suspension polymerization of a water-soluble ethylenically unsaturated monomer using a radical polymerization initiator in a hydrocarbon dispersion medium, wherein the water-absorbent resin has the following characteristics (1) to (3):

(1) the water-retention capacity of physiological saline thereof is 38 g/g or more,
(2) the water-absorption capacity of physiological saline under a load of 4.14 kPa thereof is 15 ml/g or more, and (3) the tan δ of a 50-fold swollen gel thereof is $2.10 \times 10^{-2}$ or more.

Item 2. The water-absorbent resin according to item 1, wherein the water-soluble ethylenically unsaturated monomer is at least one selected from the group consisting of (meth)acrylic acid and salts thereof, (meth)acrylamide, and N,N-dimethylacrylamide.

Item 3. The water-absorbent resin according to item 1 or 2, wherein the water-absorbent resin is crosslinked with an internal-crosslinking agent and a post-crosslinking agent.

Item 4. The water-absorbent resin according to item 3, wherein the amount of the internal-crosslinking agent to be used is 0.000015 to 0.00020 mol per mol of the water-soluble ethylenically unsaturated monomer subjected to the polymerization and the amount of the post-crosslinking agent to be used is 0.00025 to 0.0010 mol per mol of the water-soluble ethylenically unsaturated monomer subjected to the polymerization.

Item 5. The water-absorbent resin according to item 3 or 4, wherein the internal-crosslinking agent and the post-crosslinking agent are polyglycidyl compounds.

Item 6. An absorbent material comprising the water-absorbent resin according to any one of items 1 to 5 and hydrophilic fibers.

Item 7. An absorbent article wherein the absorbent material according to item 6 is held between a liquid-permeable sheet and a liquid-impermeable sheet.

Item 8. A method for producing a water-absorbent resin, wherein the water-absorbent resin has the following characteristics (1) to (3):

(1) the water-retention capacity of physiological saline thereof is 38 g/g or more, (2) the water-absorption capacity of physiological saline under a load of 4.14 kPa thereof is 15 ml/g or more, and (3) the tan δ of a 50-fold swollen gel thereof is $2.10 \times 10^{-2}$ or more, and wherein the method includes a first step and a second step each defined below:

the first step of performing reversed phase suspension polymerization of a water-soluble ethylenically unsaturated monomer in the presence of a radical polymerization initiator and an internal-crosslinking agent in a hydrocarbon dispersion medium; and the second step of crosslinking suspension polymerized particles obtained in the first step with a post-crosslinking agent.

Item 9. The method for producing a water-absorbent resin according to item 8, wherein the water-soluble ethylenically unsaturated monomer is at least one selected from the group consisting of (meth)acrylic acid and salts thereof, (meth)acrylamide, and N,N-dimethylacrylamide.

Item 10. The method for producing a water-absorbent resin according to item 8 or 9, wherein the amount of the internal-crosslinking agent to be used in the first step is 0.000015 to 0.00020 mol per mol of the water-soluble ethylenically unsaturated monomer subjected to the polymerization and the amount of the post-crosslinking agent used in the second step is 0.00025 to 0.0010 mol per mol of the water-soluble ethylenically unsaturated monomer subjected to the polymerization.

Item 11. The method for producing a water-absorbent resin according to any one of items 8 to 10, wherein the internal-crosslinking agent and the post-crosslinking agent are polyglycidyl compounds.

Advantages of the Invention

By fulfilling specific ranges of water-retention capacity of physiological saline, water-absorption capacity of physiological saline under a load of 4.14 kPa, and tan δ of a 50-fold swollen gel, the water-absorbent resin of the present invention can make an absorbent material comprising the water-absorbent resin have excellent shape retention property and therefore can suppress deformation of the absorbent material and prevent cracking or uneven distribution when having been used for a hygienic material even if compression or a shearing force is applied due to the motion of a wearer. Moreover, the water-absorbent resin of the present invention can make an absorbent material comprising the water-absorbent resin possess excellent absorption performance, have a high liquid permeation rate, and suppress re-wet of a liquid having been absorbed, by fulfilling the above-described properties.

Thus, the water-absorbent resin of the present invention is excellent in water absorption performance and therefore can be used for an absorbent material and an absorbent article for various applications. Especially, the water-absorbent resin of the present invention can be used suitably for a hygienic material such as a disposable diaper.

EMBODIMENTS OF THE INVENTION

Figure 1:
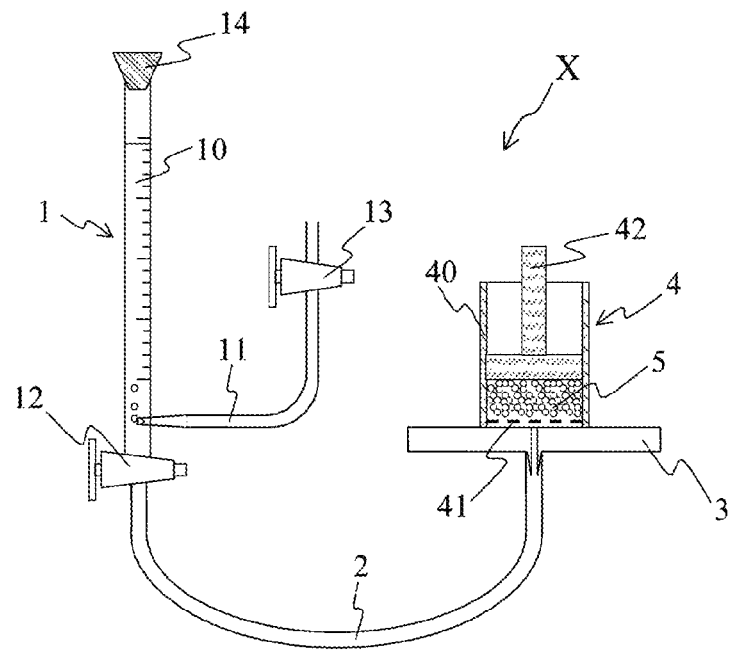
FIG. 1 is a schematic diagram illustrating a schematic arrangement of an apparatus for measuring the water-absorption capacity of physiological saline under a load of 4.14 kPa of a water-absorbent resin.

The water-absorbent resin of the present invention is a water-absorbent resin obtained by performing reversed phase suspension polymerization of a water-soluble ethylenically unsaturated monomer using a radical polymerization initiator in a hydrocarbon dispersion medium and is characterized by having the following characteristics (1) to (3):

(1) the water-retention capacity of physiological saline thereof is 38 g/g or more, (2) the water-absorption capacity of physiological saline under a load of 4.14 kPa thereof is 15 ml/g or more, and (3) the tan δ of a 50-fold swollen gel thereof is $2.10 \times 10^{-2}$ or more.

In the following, a concrete description is made to the water-absorbent resin of the present invention.

Characteristics of Water-absorbent Resin (1) Water-retention Capacity of Physiological Saline The water-retention capacity of physiological saline of the water-absorbent resin of the present invention is 38 g/g or more, preferably 40 g/g or more. The water-retention capacity of physiological saline does not have any particular upper limit, but it is, for example, 60 g/g or less, preferably 50 g/g or less, more preferably 47 g/g or less. The water-retention capacity of physiological saline is preferably 38 to 60 g/g, more preferably 40 to 50 g/g, even more preferably 40 to 47 g/g. The water-retention capacity of physiological saline of a water-absorbent resin is a value measured in accordance with the measurement method disclosed in "Water-retention capacity of physiological saline" described below.

(2) Water-absorption Capacity of Physiological Saline under a Load

The water-absorption capacity of physiological saline under a load of 4.14 kPa of the water-absorbent resin of the present invention is 15 mL/g or more, preferably 18 ml/g or more, more preferably is 21 ml/g or more. The water-absorption capacity of physiological saline under a load does not have any particular upper limit, but it is, for example, 30 mL/g or less, preferably 28 mL/g or less, more preferably 25 mL/g or less. The water-absorption capacity of physiological saline under a load is preferably 18 to 30 mL/g, more preferably 21 to 28 mL/g, even more preferably 21 to 25 mL/g. The water-absorption capacity of physiological saline under a load of 4.14 kPa of a water-absorbent resin is a value measured in accordance with the measurement method disclosed in "Water-absorption capacity of physiological saline under a load of 4.14 kPa" described below.

(3) Viscoelasticity at the Time of Swelling

The tan δ of a gel obtained by swelling the water-absorbent resin of the present invention to 50 times with physiological saline is $2.10 \times 10^{-2}$ or more, preferably $2.15 \times 10^{-2}$ or more. The tan δ does not have any particular upper limit, but it is, for example, $2.80 \times 10^{-2}$ or less, preferably $2.40 \times 10^{-2}$ or less. The tan δ is preferably $2.10 \times 10^{-2}$ to $2.80 \times 10^{-2}$, more preferably $2.15 \times 10^{-2}$ to $2.40 \times 10^{-2}$.

Details of tan δ are described, for example, at pages 28 to 34 of "Viscoelasticity of Polymers" (John D. Ferry, translated by Hiroshi SOFUE (supervisor), Jokichi MURAKAMI, and Masao TAKAHASHI, published by Tokyo Kagaku Dojin, October, 1964). Generally, in viscoelasticity evaluation, a macromolecular material is expressed by a model composed of an elastic component and a viscous component. The former is a component that converts impact energy into repulsion energy and the latter is a component that converts impact energy into dissipation energy. In dynamic viscoelasticity analysis with oscillatory strain, a complex modulus $G^* = G' + iG''$ (i is an imaginary unit) is indicated physically. Herein, G' (storage modulus) and G'' (loss modulus) denote the size of the elastic component and the size of the viscous component of the macromolecular material, respectively. Tan δ (loss tangent)=G''/G' is an index of energy to be lost when the material deforms. The viscoelasticity at the time of swelling of a water-absorbent resin (tan δ of a gel swollen to 50 times with physiological saline) is a value measured in accordance with the measurement method disclosed in "tan δ of 50-fold swollen gel" described below.

The water-absorbent resin of the present invention satisfies the aforementioned characteristics (1) to (3) and thereby allows an absorbent material comprising the water-absorbent resin to be inhibited from cracking or unevenly distributing even if compression or a shearing force is applied with the absorbent material having absorbed a liquid, so that the absorbent material is allowed to retain its shape stably and can possess excellent shape retention property. In addition, the water-absorbent resin of the invention satisfies the aforementioned three characteristics and thereby allows an absorbent material comprising the water-absorbent resin to possess excellent absorption performance, and the absorbent material has a large capacity for liquid absorption and an increased rate of liquid permeation and be allowed to suppress a gel blocking phenomenon, which is likely to occur upon absorption of a liquid, and retain its absorption performance stably. The "gel blocking phenomenon" as referred to herein is a phenomenon in which when a large amount of water-absorbent resin has been used for an absorbent material, a large amount of water-absorbent resin located in or near a surface layer absorbs a liquid and a soft gel thereby becomes denser in or near the surface layer, so that permeation of a liquid into the water-absorbent resin is inhibited and the water-absorbent resin thereby becomes impossible to absorb a liquid efficiently. Moreover, the water-absorbent resin of the present invention satisfies the aforementioned characteristics (1) to (3) and thereby allows an absorbent material comprising the water-absorbent resin to have an improved action to retain a liquid having been absorbed, so that re-wet of a liquid due to deformation, compression, or the like can be suppressed.

The median particle size of the water-absorbent resin of the invention is not particularly limited, but, for example, it is 200 to 600 μm, preferably 250 to 550 μm, more preferably 300 to 500 μm. The median particle size of a water-absorbent resin is a value measured in accordance with the measurement method disclosed in the "Median particle size" described below.

Method for Producing Water-absorbent Resin

The water-absorbent resin of the present invention can be obtained by performing reversed phase suspension polymerization of a water-soluble ethylenically unsaturated monomer using a radical polymerization initiator in a hydrocarbon dispersion medium and thereby controlling the crosslinking density of suspension polymerized particles into a prescribed range. More specifically, the water-absorbent resin of the present invention can be obtained via the following first and second steps; the first step of performing reversed phase suspension polymerization of a water-soluble ethylenically unsaturated monomer in the presence of a radical polymerization initiator and a prescribed amount of an internal-crosslinking agent in a hydrocarbon dispersion medium, and the second step of crosslinking the suspension polymerized particles obtained in the first step with a prescribed amount of a post-crosslinking agent.

In the following, a detailed description is made to the first step and the second step.

<First step>

In the first step, suspension polymerized particles are obtained by performing reversed phase suspension polymerization of a water-soluble ethylenically unsaturated monomer in the presence of a radical polymerization initiator and a prescribed amount of an internal-crosslinking agent in a hydrocarbon dispersion medium.

[Water-soluble Ethylenically Unsaturated Monomer]

The water-soluble ethylenically unsaturated monomer to be used as a raw material is not particularly restricted; examples thereof include (meth)acrylic acid (in the present specification, "acryl" and "methacryl" are expressed collectively as "(meth)acryl"; the same applies hereinafter) and salts thereof; 2-(meth)acrylamido-2-methylpropanesulfonic acid and salts thereof; nonionic monomers such as (meth)acrylamide, N,N-dimethyl(meth)acrylamide, 2-hydroxyethyl(meth)acrylate, N-methylol(meth)acrylamide, and polyethylene glycol mono(meth)acrylate; and amino group-containing unsaturated monomers such as N,N-diethylaminoethyl(meth)acrylate, N,N-diethylaminopropyl(meth)acrylate, and diethylaminopropyl(meth)acrylamide, and quaternary compounds thereof. Such water-soluble ethylenically unsaturated monomers may be used alone or in combination of two or more kinds.

Among those water-soluble ethylenically unsaturated monomers, preferred are (meth)acrylic acid and salts thereof, (meth)acrylamide, and N,N-dimethylacrylamide; more preferred are (meth)acrylic acid and salts thereof, and acrylamide.

The water-soluble ethylenically unsaturated monomer may be used in the form of an aqueous solution in order to increase dispersion efficiency in a hydrocarbon dispersion medium at the time of performing reversed phase suspension polymerization. The concentration of the monomer in such an aqueous solution is not particularly limited; usually, it is only required to be not lower than 20% by mass but not higher than the saturation concentration, and it is preferably 25 to 70% by mass, more preferably 30 to 55% by mass.

When the water-soluble ethylenically unsaturated monomer has an acid group like (meth)acrylic acid, 2-(meth) acrylamido-2-methylpropanesulfonic acid, or the like, the acid group may have been neutralized with an alkaline neutralizing agent. As such an alkaline neutralizing agent, sodium hydroxide, potassium hydroxide, ammonia, and so on can be used. Such alkaline neutralizing agents may be used alone or in combination of two or more kinds.

The degree of neutralization of the acid groups of the water-soluble ethylenically unsaturated monomer attained with an alkaline neutralizing agent may be determined so as to enhance the water absorption capacity of a resulting water-absorbent resin by increasing the osmotic pressure of the resin and so as not to cause problems with safety, etc., due to the presence of an excess of the alkaline neutralizing agent; it is, for example, 10 to 100 mol %, preferably 30 to 80 mol %.

[Hydrocarbon Dispersion Medium]

The hydrocarbon dispersion medium is not particularly restricted as long as it is a hydrocarbon compound capable of being used as a dispersion medium in reversed phase suspension polymerization of a water-soluble ethylenically unsaturated monomer; examples thereof include aliphatic hydrocarbon, such as n-hexane, n-heptane, 2-methylhexane, 3-methylhexane, 2,3-dimethylpentane, 3-ethylpentane, and n-octane; alicyclic hydrocarbons, such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons, such as benzene, toluene and xylene. Among these hydrocarbon dispersion mediums, n-hexane, n-heptane, and cyclohexane are preferred from the viewpoint of being easily available industrially, stable in quality, and inexpensive. Such hydrocarbon dispersion mediums may be used alone or in combination of two or more kinds. Preferable examples of mixtures of the hydrocarbon dispersion mediums include Exxsol Heptane (produced by ExxonMobil Chemical; containing 75 to 85% by mass of heptane and its isomeric hydrocarbons), which is commercially available.

The amount of the hydrocarbon dispersion medium to be used is usually 50 to 600 parts by mass, preferably 80 to 550 parts by mass, relative to 100 parts by mass of the water-soluble ethylenically unsaturated monomer from the viewpoint of making it easier to control polymerization temperature by removing heat of polymerization.

[Radical Polymerization Initiator]

Examples of the radical polymerization initiator include persulfates, such as potassium persulfate, ammonium persulfate, and sodium persulfate; peroxides, such as methyl ethyl ketone peroxide, methyl isobutyl ketone peroxide, di-tert-butyl peroxide, tert-butyl cumyl peroxide, tert-butyl peroxyacetate, tert-butyl peroxyisobutyrate, tert-butyl peroxypivalate, and hydrogen peroxide; and azo compounds, such as 2,2'-azobis(2-amidinopropane)dihydrochloride, 2,2'-azobis[2-(N-phenylamidino)propane]dihydrochloride, 2,2'-azobis[2-(N-allylamidino)propane]dihydrochloride, 2,2'-azobis{2-[1-(2-hydroxyethyl)-2-imidazolin-2-yl] propane}dihydrochloride, 2,2'-azobis{2-methyl-N-[1,1-bis (hydroxymethyl)-2-hydroxyethyl]propionamide}, 2,2'-azobis[2-methyl-N-(2-hydroxyethyl)-propionamide], and 4,4'-azobis(4-cyanovaleric acid). Among these radical polymerization initiators, potassium persulfate, ammonium persulfate, sodium persulfate, and 2,2'-azobis(2-amidinopropane)dihydrochloride are preferred from the viewpoint of easy availability and easy handleability. Such radical polymerization initiators may be used alone or in combination of two or more kinds.

The aforementioned radical polymerization initiator may also be used in combination with a reducing agent, such as sodium sulfite, sodium hydrogensulfite, ferrous sulfate, and L-ascorbic acid, and thereby used as a redox polymerization initiator.

The amount of the radical polymerization initiator to be used is not particularly limited, but, for example, is 0.00005 to 0.01 mol per mol of the water-soluble ethylenically unsaturated monomer. Satisfaction of such an amount used can avoid occurrence of a rapid polymerization reaction and can complete a polymerization reaction within an appropriated time.

[Internal-crosslinking Agent]

The internal-crosslinking agent is used in order to afford an appropriate crosslinking density to suspension polymerized particles and impart excellent water absorption performance to a resulting water-absorbent resin.

The internal-crosslinking agent is not particularly restricted with respect to the type thereof as long as it can crosslink suspension polymerized particles; examples thereof include unsaturated polyesters obtained by reacting polyols, such as diols and triols, e.g., (poly)ethylene glycol ["(poly)" means both a case with a prefix "poly" and a case without the prefix; the same applies hereinafter], (poly) propylene glycol, 1,4-butanediol, trimethylolpropane, and (poly)glycerin, with unsaturated acids, such as (meth)acrylic acid, maleic acid, and fumaric acid; bisacrylamides such as N,N-methylenebisacrylamide; di or tri(meth)acrylic acid esters obtained by reacting a polyepoxide with (meth)acrylic acid; carbamyl di(meth)acrylates obtained by reacting a polyisocyanate, such as tolylene diisocyanate and hexamethylene diisocyanate, with hydroxyethyl(meth)acrylate; compounds having two or more polymerizable unsaturated groups, such as allylated starch, allylated cellulose, diallyl phthalate, N,N',N"-triallylisocyanate, and divinylbenzene; polyglycidyl compounds such as diglycidyl compounds and triglycidyl compounds, e.g., (poly)ethylene glycol diglycidyl ether, (poly)propylene glycol diglycidyl ether, and (poly)glycerin diglycidyl ether; epihalohydrin compounds such as epichlorohydrin, epibromohydrin, and α-methyl-epichlorohydrin; compounds having two or more reactive functional groups, such as isocyanate compounds, e.g., 2,4-tolylene diisocyanate and hexamethylene diisocyanate; and oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol. Among these internal-crosslinking agents, polyglycidyl compounds are preferred, diglycidyl ether compounds are more preferred, and (poly) ethylene glycol diglycidyl ether is even more preferred. Such internal-crosslinking agents may be used alone or in combination of two or more kinds.

Although the amount of the internal-crosslinking agent to be used may be determined to 0.000015 to 0.00020 mol per mol of the water-soluble ethylenically unsaturated monomer subjected to polymerization, the amount used is preferably 0.000020 to 0.000150 mol, more preferably 0.000030 to 0.000080 mol. By use of the internal-crosslinking agent in such a range, excellent water absorption performance can be imparted to a resulting water-absorbent resin.

[Dispersion Stabilizer]

In the reversed phase suspension polymerization to be performed in the first step, a dispersion stabilizer may be used as necessary in order to stabilize the dispersion of the water-soluble ethylenically unsaturated monomer. Examples of the dispersion stabilizer include surfactants. Specific examples of the surfactant to be used as a dispersion stabilizer include nonionic surfactants such as sorbitan fatty acid esters, polyglycerin fatty acid esters, sucrose fatty acid esters, sorbitol fatty acid esters, and polyoxyethylene alkyl phenyl ethers; and anionic surfactants such as fatty acid salts, alkylbenzene sulfonates, alkyl methyl taurates, polyoxyethylene alkyl phenyl ether sulfates, and polyoxyethylene alkyl ether sulfonates. Among these surfactants, sorbitan fatty acid esters, polyglycerin fatty acid esters, and sucrose fatty acid esters are preferred from the viewpoint of dispersion stability of a water-soluble ethylenically unsaturated monomer. Such surfactants may be used alone or in combination of two or more kinds.

Although the amount of the surfactant to be used may be determined appropriately as long as the dispersion state of the water-soluble ethylenically unsaturated monomer in the hydrocarbon dispersion medium can be kept good and a dispersion effect commensurate with the amount used can be attained, the amount used is, for example, 0.1 to 5 parts by mass, preferably 0.2 to 3 parts by mass, relative to 100 parts by mass of the water-soluble ethylenically unsaturated monomer.

A polymeric dispersion agent may be used as a dispersion stabilizer in combination with a surfactant. Examples of the polymeric dispersion agent to be used include ethylcellulose, ethylhydroxyethylcellulose, polyethylene oxide, maleic anhydride modified polyethylene, maleic anhydride modified ethylene-propylene copolymers, maleic anhydride modified polybutadiene, and maleic anhydride modified EPDM (ethylene-propylene-diene terpolymers).

Although the amount of the polymeric dispersion agent to be used may be determined appropriately as long as the dispersion state of the water-soluble ethylenically unsaturated monomer in the hydrocarbon dispersion medium can be kept good and a dispersion effect commensurate with the amount used can be attained, the amount used is, for example, 0.1 to 5 parts by mass, preferably 0.2 to 3 parts by mass, relative to 100 parts by mass of the water-soluble ethylenically unsaturated monomer.

Moreover, a thickener may be used as a dispersion stabilizer. Examples of the thickener to be used as a dispersion stabilizer include hydroxyethylcellulose, hydroxypropylcellulose, methylcellulose, carboxymethylcellulose, polyacrylic acid, (partially) neutralized polyacrylic acid, polyethylene glycol, polyacrylamide, polyethyleneimine, dextrin, sodium alginate, poly(vinyl alcohol), polyvinylpyrrolidone, and polyethylene oxide.

[Conditions for Reversed Phase Suspension Polymerization Reaction]

The reversed phase suspension polymerization in the first step is carried out by adding a water-soluble ethylenically unsaturated monomer, a radical polymerization initiator, an internal-crosslinking agent, and, as necessary, a dispersion stabilizer in prescribed amounts into a hydrocarbon dispersion medium and then heating them.

The reaction temperature of the reversed phase suspension polymerization varies depending upon the type of the radical polymerization initiator to be used and therefore cannot be equally defined, but it is usually 20 to 110° C., preferably 40 to 80° C. Setting to such a reaction temperature makes it possible to perform a smooth polymerization reaction by removing heat of polymerization while suppressing the polymerization time to be elongated.

The reaction time of the reversed phase suspension polymerization, which may be determined appropriately with consideration given to the type and amount of the raw material compounds to be used, the reaction temperature, and so on, is usually 0.5 to 4 hours.

The reversed phase suspension polymerization in the first step may be performed either in a single stage or in two or more multiple stages. The number of the stages is preferably two or three from the viewpoint of improving production efficiency.

When reversed phase suspension polymerization with two or more stages is performed, this can be performed by carrying out the first stage reversed phase suspension polymerization in the above-described method, followed by addition and mixing of a water-soluble ethylenically unsaturated monomer to the reaction mixture obtained in the first stage polymerization reaction, and then carrying out the second or later stage reversed phase suspension polymerization in the same method as that for the first stage. In the reversed phase suspension polymerization in each of the second or later stages, the reversed phase suspension polymerization can be performed under the same conditions as those for the above-described method by adding a radical polymerization initiator, an internal-crosslinking agent and so on in addition to the water-soluble ethylenically unsaturated monomer within ranges of the molar ratios of the individual components relative to the above-described water-soluble ethylenically unsaturated monomer based on the amount of the water-soluble ethylenically unsaturated monomer to be added in the reversed phase suspension polymerization in each of the second or later stages.

<Second step>

In the second step, the suspension polymerized particles obtained in the first step are subjected to post-crosslinking treatment with a post-crosslinking agent. By thus subjecting the suspension polymerized particles to post-crosslinking treatment with a post-crosslinking agent, moderate crosslinking is applied to the suspension polymerized particles obtained in the first step, so that excellent water absorption performance can be imparted to a water-absorbent resin.

The post-crosslinking agent is not particularly restricted as long as it can react with functional groups (e.g., a carboxyl group) of the water-absorbent resin; examples thereof include polyols, such as (poly)ethylene glycol, (poly)propylene glycol, 1,4-butanediol, trimethylolpropane, and (poly)glycerin; polyglycidyl compounds, such as diglycidyl compounds, e.g., (poly)ethylene glycol diglycidyl ether, (poly)propylene glycol diglycidyl ether, and (poly) glycerin diglycidyl ether, triglycidyl compounds, e.g., (poly) ethylene glycol triglycidyl ether, (poly)propylene glycol triglycidyl ether, and (poly)glycerin triglycidyl ether, and tri- or more valent glycidyl compounds such as (poly)propylene glycol polyglycidyl ether and (poly)glycerin polyglycidyl ether; haloepoxy compounds, such as epichlorohydrin, epibromohydrin, and α-methylepichlorohydrin; compounds having two or more reactive functional groups, such as isocyanate compounds, e.g., 2,4-tolylene diisocyanate and hexamethylene diisocyanate; oxetane compounds, such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol; oxazoline compounds, such as 1,2-ethylenebisoxazoline; and carbonate compounds, such as ethylene carbonate. Among these post-crosslinking agents, polyglycidyl compounds are preferred, diglycidyl compounds are more preferred, and (poly)ethylene glycol diglycidyl ether is even more preferred. Such post-crosslinking agents may be used alone or in combination of two or more kinds.

Although the amount of the post-crosslinking agent to be used may be determined to 0.00025 to 0.0010 mol per mol of the total amount of the water-soluble ethylenically unsaturated monomer used for the reversed phase suspension polymerization of the first step, the amount used is preferably 0.00044 to 0.00080 mol, more preferably 0.00044 to 0.00076 mol. By use of a post-crosslinking agent in such a range, a moderate crosslinking density can be imparted to the suspension polymerized particles obtained in the first step, so that excellent water absorption performance can be imparted to a resulting water-absorbent resin.

The time at which the post-crosslinking agent is added may be any time after the completion of the first step and is not particularly limited. At the time of adding a post-crosslinking agent, it is preferable to add the agent in the presence of water in an amount within the range of 1 to 400 parts by mass relative to the total amount of 100 parts by mass of the water-soluble ethylenically unsaturated monomer used for obtaining the water-absorbent resin, it is more preferable to add the agent in the presence of water in an amount within the range of 5 to 200 parts by mass, and it is even more preferable to add the agent in the presence of water in an amount within the range of 10 to 100 parts by mass.

At the time of adding a post-crosslinking agent, it is also permitted to use a solvent such as water and a hydrophilic organic solvent. Examples of the hydrophilic organic solvent to be used as the solvent for the post-crosslinking treatment include lower alcohols, such as methanol, ethanol, n-propanol, and isopropanol; ketones, such as acetone and methyl ethyl ketone; ethers, such as diethyl ether, dioxane, and tetrahydrofuran; amides, such as N,N-dimethylformamide; and sulfoxides, such as dimethylsulfoxide. Such hydrophilic organic solvents may be used alone or in combination of two or more kinds. As to the solvent to be used for the post-crosslinking treatment, it is permitted to use only one of water and a hydrophilic organic solvent or alternatively it is permitted to use a mixture of water and a hydrophilic organic solvent.

Although the reaction temperature of the post-crosslinking treatment is not particularly limited, it is, for example, 50 to 250° C., preferably 60 to 180° C., more preferably 60 to 140° C., even more preferably 70 to 120° C.

The reaction time of the post-crosslinking treatment varies depending upon the reaction temperature, the type and the amount of the post-crosslinking agent used, and so on and therefore cannot be equally defined, but it is usually 1 to 300 minutes, preferably 5 to 200 minutes.

By performing the first step and the second step in such a manner, there is produced a water-absorbent resin being excellent in water absorption performance and capable of improving the shape retention property of an absorbent material when being used for the absorbent material.

The water-absorbent resin can be collected after the second step by removing the hydrocarbon dispersion medium and the solvent. The method for removing the hydrocarbon dispersion medium and the solvent is not particularly restricted, and it may be drying treatment, for example. The drying treatment may be performed either under normal pressure or under reduced pressure. The drying treatment may be performed under a flow of nitrogen or the like in order to enhance drying efficiency. When the drying treatment is performed under normal pressure, the drying temperature is, for example, 70 to 250° C., preferably 80 to 180° C., more preferably 80 to 140° C., even more preferably 90 to 130° C. When the drying treatment is performed under reduced pressure, the drying temperature is, for example, 60 to 100° C., preferably 70 to 90° C.

Absorbent Material and Absorbent Article

The absorbent material of the present invention is an item composed of the above-described water-absorbent resin of the present invention and a hydrophilic fiber. The configuration of the absorbent material is not particularly limited; examples thereof include a mixing structure in which a water-absorbent resin and hydrophilic fibers are blended uniformly, a sandwich structure in which a water-absorbent resin is held between layered hydrophilic fibers, and a structure in which a water-absorbent resin and hydrophilic fibers are wrapped with a wrapping sheet such as tissue paper.

The hydrophilic fibers are not particularly restricted; examples thereof include cellulose fibers, such as cotton-like pulp obtained from wood, mechanical pulp, chemical pulp, and semi-chemical pulp; artificial cellulose fibers, such as rayon and acetate; and fibers made of synthetic resins, such as hydrophilized polyamide, polyester, or polyolefin.

Moreover, in the absorbent material of the present invention, a thermally fused synthetic fibers for enhancing the shape retention property of the absorbent material, a hot melt adhesive, or an adhesive binder such as an adhesive emulsion may, as necessary, have been added in addition to the water-absorbent resin and the hydrophilic fibers.

Although the content of the water-absorbent resin in the absorbent material of the present invention is not particularly limited, it is, for example, 30 to 85% by mass, preferably 40 to 80% by mass, more preferably 45 to 70% by mass. Fulfillment of the aforementioned content by the water-absorbent resin leads to a large liquid absorption capacity of the absorbent material and can suppress leakage or re-wet of a liquid and also can attain good comfort in use.

The above-described absorbent material of the present invention can be fabricated into an absorbent article by holding it between a liquid-permeable sheet that allows a liquid to pass therethrough (a top sheet) and a liquid-impermeable sheet that does not allow a liquid to pass therethrough (a back sheet). The liquid-permeable sheet is disposed on a side where the sheet comes into contact with the body and the liquid-impermeable sheet is disposed on the side opposite from the side where the sheet comes into contact with the body.

Examples of the liquid-permeable sheet include air-through, spunbond, chemical bond, or needle punch nonwoven fabrics made of fibers of polyethylene, polypropylene, polyester, or the like and porous synthetic resin sheets, or the like.

Examples of the liquid-impermeable sheet include synthetic resin films made of resins such as polyethylene, polypropylene, and polyvinyl chloride.

The type of the absorbent article is not particularly restricted; examples thereof include hygienic materials such as disposable diapers, sanitary napkins, and incontinent pads; urine-absorbent materials for pets; materials for civil engineering and construction such as packing materials; food freshness retaining materials such as drip absorbents and cold-reserving agents; and agricultural and horticultural articles such as water-retaining materials for soils. Among these, hygienic materials are suitable as the absorbent article of the present invention because hygienic materials are used in contact with human bodies and therefore they are required to have excellent comfort in use (a high liquid permeation rate and a little amount of re-wet of liquid) and durability (shape retention property) against compression or a shearing force to be applied when the materials are worn.

EXAMPLES

The present invention is described in more detail below by way of examples and comparative examples, but the present invention is not limited only to the examples.

For the water-absorbent resins obtained in each of the examples and the comparative examples, water-retention capacity of physiological saline, water-absorption capacity of physiological saline under a load of 4.14 kPa, tan δ of a 50-fold swollen gel, and a median particle size were measured by the methods described below.

<Water-retention Capacity of Physiological Saline>

500 g of a 0.9% by mass aqueous solution of sodium chloride (physiological saline) was weighed out into a 500-mL beaker, and then 2.0 g of water-absorbent resin was dispersed therein with stirring of 600 rpm so as not to form lumps. The dispersion was left to stand for 30 minutes with agitation, so that the water-absorbent resin was swollen sufficiently. Subsequently, the dispersion was poured into a cotton bag (Cottonbroad No. 60, 100 mm in width and 200 mm in length), and the upper part of the cotton bag was closed with a rubber band. The cotton bag was dehydrated for 1 minute by using a dehydrator (produced by Kokusan Co., Ltd., product number: H-122) that had been set at a centrifugal force of 167 G, and the mass Wa (g) of the dehydrated cotton bag containing swollen gel was measured. The same procedure was repeated without adding the water-absorbent resin, and the mass Wb (g) of the empty cotton bag upon wetting was measured. The water-retention capacity was calculated by the following equation:

Water-retention capacity of physiological saline (g/g)=[Wa−Wb](g)/the mass (g) of water-absorbent resin <Water-absorption Capacity of Physiological Saline under a Load of 4.14 kPa>

The water-absorption capacity of physiological saline under a load of 4.14 kPa of a water-absorbent resin was measured by using a measurement apparatus X whose schematic configuration is illustrated in FIG. 1.

The measurement apparatus X depicted in FIG. 1 includes a burette section 1, a lead tube 2, a measuring platform 3, and a measuring section 4 put on the measuring platform 3. The burette section 1 is connected to a rubber plug 14 on the top portion of a burette 10 and also connected to an air inlet tube 11 and a cock 12 at the bottom portion, and a cock 13 is placed at the top portion of the air inlet tube 11. The burette section 1 and the measuring platform 3 are linked via the lead tube 2 attached thereto. The lead tube 2 has a diameter of 6 mm There is a hole with a diameter of 2 mm at the central section of the measuring platform 3 and the lead tube 2 is connected thereto. The measuring section 4 has a cylinder 40, a nylon mesh 41 adhered to the bottom part of the cylinder 40, and a weight 42. The cylinder 40 has an inner diameter of 2.0 cm. The 200-mesh (75 μm in mesh size) nylon mesh 41 is configured so that a prescribed amount of water-absorbent resin 5 is evenly spread thereon. The weight 42 has a diameter of 1.9 cm and a mass of 119.6 g. This weight 42 is configured to be put on the water-absorbent resin 5 and apply a load of 4.14 kPa evenly to the water-absorbent resin 5.

In the measurement apparatus X with such configuration, the cock 12 and the cock 13 at the burette section 1 are closed first, and a physiological saline adjusted to 25° C. is poured from the top of the burette 10 and the top of the burette is then plugged tightly with the rubber plug 14. Thereafter, the cock 12 and the cock 13 at the burette section 1 are opened. Next, the height of the measuring platform 3 is adjusted so that the end of the lead tube 2 at the central section of the measuring platform 3 and an air introduction port of the air inlet tube 11 may be at the same height.

On the other hand, 0.10 g of the water-absorbent resin 5 is evenly spread over the nylon mesh 41 in the cylinder 40, and the weight 42 is put on the water-absorbent resin 5. The measuring section 4 is put so that its center may be in alignment with a lead tube port in the central part of the measuring platform 3.

The volume decrease of the physiological saline in the burette 10, i.e., the volume of the physiological saline absorbed by the water-absorbent resin 5, Wc (mL), is continuously read off from the time point when the water-absorbent resin 5 started absorbing water. The water-absorption capacity of physiological saline under a load of 4.14 kPa of the water-absorbent resin 5 at the time 60 minutes after the start of water absorption was determined from the following equation.

Water-absorption capacity of physiological saline under a load of 4.14 kPa (mL/g)=Wc(mL)÷0.10 (g)

<Tan δ of 50-fold Swollen Gel>

A gel resulting from swelling of a water-absorbent resin to 50 times with physiological saline (50-fold swollen gel) was prepared by the method described below. 49.0 g of physiological saline was weighed out into a 100 mL beaker, then a magnetic stirrer bar (8 mm in diameter and 30 mm in length, having no rings) was put in. Then, the beaker was put on a magnetic stirrer (produced by Iuchi; HS-30D) and the magnetic stirrer bar was controlled to rotate at 600 rpm. Subsequently, 1.0 g of a water-absorbent resin was put into the beaker under stirring, and the stirring was continued until the rotation vortex disappeared and the liquid surface became flat, so that a 50-fold swollen gel was prepared. The 50-fold swollen gel was moved to a centrifugation tube and then degassed by treating it for 4 minutes with a centrifuge (Kokusan Co., Ltd., product number: H-103NA SERIES) that had been set at a centrifugal force of 671 G. Thus, a sample to be measured was prepared.

In measurement, distribution with respect to frequency omega (rad/second) of storage modulus G' (Pa) and that of loss modulus G" (Pa) were measured with a dynamic viscoelasticity measuring device, rheometer (produced by TA Instruments Japan Inc., product No. AR2000eZ). Parallel plates with a diameter of 60 mm were used as a sample holder and the distance between the plates was adjusted to 3 mm. The measurement temperature was set to 25±2° C., and G' and G" were measured within a range of frequency omega of 0.1 to 300 rad/sec. Then, a value of tan δ at 10 rad/sec was calculated from the ratio of G' to G" and the value was defined to be tan δ of the 50-fold swollen gel of the water-absorbent resin.

<Median Particle Size>

0.25 g of amorphous silica (Degussa Japan, Sipernat 200) was mixed as a lubricant with 50 g of a water-absorbent resin.

This mixture was made to pass through a JIS standard sieve having a mesh size of 250 μm, and then the median particle size was measured by using sieve combination <A> when the amount of the remainder left on the sieve was less than 50% by mass of the mixture or by using sieve combination <B> when the amount of the remainder was 50% by mass or more.

<A> JIS standard sieves, a sieve having a mesh size of 425 μm, a sieve having a mesh size of 250 μm, a sieve having a mesh size of 180 μm, a sieve having a mesh size of 150 μm, a sieve having a mesh size of 106 μm, a sieve having a mesh size of 75 μm, a sieve having a mesh size of 45 μm, and a receiving tray, were combined in order from the top.

<B> JIS standard sieves, a sieve having a mesh size of 850 μm, a sieve having a mesh size of 600 μm, a sieve having a mesh size of 500 μm, a sieve having a mesh size of 425 μm, a sieve having a mesh size of 300 μm, a sieve having a mesh size of 250 μm, a sieve having a mesh size of 150 μm, and a receiving tray, were combined in order from the top.

The above-mentioned water-absorbent resin was placed on the uppermost sieve of the combined sieves, and shaken for 20 minutes with a rotating and tapping shaker machine to classify the resin.

After classification, the relationships between the mesh size of the sieve and an integral of a mass percentage of the water-absorbent resin remaining on the sieve were plotted on a logarithmic probability paper by calculating the mass of the water-absorbent resin remaining on each sieve as a mass percentage to an entire amount, and accumulating the mass percentages in order, starting from those having larger particle diameters. The plots on the probability paper were connected by straight lines and then a particle size corresponding to a 50% by mass of the integrated mass percentage was defined as a median particle size.

Example 1

There was prepared a cylindrical round-bottomed separable flask having an internal diameter of 100 mm, equipped with a reflux condenser, a dropping funnel, a nitrogen gas inlet tube, and a stirrer having stirring blades composed of two sets of 4 inclined paddle blades with a blade diameter of 50 mm. This flask was charged with 500 mL of n-heptane, and 0.80 g of a sucrose stearate having an HLB of 3 (produced by Mitsubishi-Kagaku Foods Corporation, Ryoto sugar ester S-370) and 0.80 g of a maleic anhydride-modified ethylene-propylene copolymer (produced by Mitsui Chemicals, Inc., Hi-wax 1105A) were added thereto. The temperature was raised to 80° C. to dissolve the surfactants, and thereafter the solution was cooled to 50° C.

Separately, 92 g (1.02 mol) of an 80% by mass aqueous solution of acrylic acid was placed into another 500-mL Erlenmeyer flask, and 153.2 g of a 20% by mass aqueous solution of sodium hydroxide was added dropwise thereto with external cooling to perform 75 mol % neutralization. Thereafter, 0.28 g of hydroxyethylcellulose (Sumitomo Seika Chemicals Co. Ltd., HEC AW-15F) as a thickener, 0.07 g (0.000259 mol) of potassium persulfate as a radical polymerization initiator, and 0.011 g (0.0000631 mol) of ethylene glycol diglycidyl ether as an internal-crosslinking agent were added thereto and dissolved, so that an aqueous monomer solution for the first stage was prepared.

The above-mentioned aqueous monomer solution for the first stage was added to the above-mentioned separable flask and was kept at 35° C. for 30 minutes under replacement of the atmosphere in the system with nitrogen. Thereafter, the flask was immersed in a water bath kept at 70° C. to be heated and polymerization was carried out, so that a slurry after the first stage polymerization was obtained.

Separately, 128.8 g (1.43 mol) of an 80% by mass aqueous solution of acrylic acid was placed into another 500-mL Erlenmeyer flask, and 158.9 g of a 27% by mass aqueous solution of sodium hydroxide was added dropwise thereto with external cooling to perform 75 mol % neutralization. Thereafter, 0.10 g (0.000370 mol) of potassium persulfate as a radical polymerization initiator and 0.013 g (0.0000746 mol) of ethylene glycol diglycidyl ether as an internal-crosslinking agent were added thereto and dissolved, so that an aqueous monomer solution for the second stage was prepared.

The above-mentioned slurry after polymerization was cooled to 25° C. and the aqueous monomer solution for the second stage was added to the system and then the system was held for 30 minutes under replacement with nitrogen. The flask was immersed again in a water bath at 70° C. and the temperature was raised to perform polymerization, so that a slurry after polymerization of the second stage was obtained.

Subsequently, the temperature was raised by using an oil bath at 125° C. and 270.1 g of water was removed to the outside of the system under reflux of n-heptane by azeotropically distilling water and n-heptane, and then 9.94 g (0.00114 mol) of a 2% by mass aqueous solution of ethylene glycol diglycidyl ether was added as a post-crosslinking agent. The resulting mixture was kept at 80° C. for 2 hours and then dried by removing n-heptane, so that 231.2 g of a water-absorbent resin was obtained. The results of property measurement are shown in Table 1.

Example 2

The same operations as those of Example 1 were carried out except that the amount of water to be removed during azeotropic distillation was changed to 271.6 g and the amount of the 2% by mass aqueous solution of ethylene glycol diglycidyl ether as a post-crosslinking agent was changed to 11.04 g (0.00126 mol) in Example 1, so that 228.7 g of a water-absorbent resin was obtained. The results of property measurement are shown in Table 1.

Example 3

The same operations as those of Example 1 were carried out except that the amount of water to be removed during azeotropic distillation was changed to 273.8 g and the amount of the 2% by mass aqueous solution of ethylene glycol diglycidyl ether as a post-crosslinking agent was changed to 13.25 g (0.00152 mol) in Example 1, so that 227.4 g of a water-absorbent resin was obtained. The results of property measurement are shown in Table 1.

Example 4

The same operations as those of Example 1 were carried out except that the cooling temperature before adding the aqueous monomer solution for the second stage was changed to 23° C., the amount of water to be removed during azeotropic distillation was changed to 274.4 g and the amount of the 2% by mass aqueous solution of ethylene glycol diglycidyl ether as a post-crosslinking agent was changed to 13.25 g (0.00152 mol) in Example 1, so that 228.2 g of a water-absorbent resin was obtained. The results of property measurement are shown in Table 1.

Example 5

There was prepared a cylindrical round-bottomed separable flask having an internal diameter of 100 mm, equipped with a reflux condenser, a dropping funnel, a nitrogen gas inlet tube, and a stirrer having stirring blades composed of two sets of 4 inclined paddle blades with a blade diameter of 50 mm. This flask was charged with 500 mL of n-heptane, and 0.80 g of a sucrose stearate having an HLB of 3 (produced by Mitsubishi-Kagaku Foods Corporation, Ryoto sugar ester S-370) was added thereto. The temperature was raised to 80° C. to dissolve the surfactants, and thereafter the solution was cooled to 50° C.

Separately, 92 g (1.02 mol) of an 80% by mass aqueous solution of acrylic acid was placed into another 500-mL Erlenmeyer flask, and 153.2 g of a 20% by mass aqueous solution of sodium hydroxide was added dropwise thereto with external cooling to perform 75 mol % neutralization. Thereafter, 0.28 g of hydroxyethylcellulose (Sumitomo Seika Chemicals Co. Ltd., HEC AW-15F) as a thickener, 0.05 g (0.000184 mol) of 2,2'-azobis(2-amidinopropane)dihydrochloride as a radical polymerization initiator, and 0.006 g (0.0000344 mol) of ethylene glycol diglycidyl ether as an internal-crosslinking agent were added thereto and dissolved, so that an aqueous monomer solution for the first stage was prepared.

The above-mentioned aqueous monomer solution for the first stage was added to the above-mentioned separable flask and was kept at 35° C. for 30 minutes under replacement of the atmosphere in the system with nitrogen. Thereafter, the flask was immersed in a water bath kept at 70° C. to be heated and polymerization was carried out, so that a slurry after the first stage polymerization was obtained.

Separately, 128.8 g (1.43 mol) of an 80% by mass aqueous solution of acrylic acid was placed into another 500-mL Erlenmeyer flask, and 158.9 g of a 27% by mass aqueous solution of sodium hydroxide was added dropwise thereto with external cooling to perform 75 mol % neutralization. Thereafter, 0.07 g (0.000258 mol) of 2,2'-azobis(2-amidinopropane)dihydrochloride as a radical polymerization initiator and 0.008 g (0.0000459 mol) of ethylene glycol diglycidyl ether as an internal-crosslinking agent were added thereto and dissolved, so that an aqueous monomer solution for the second stage was prepared.

The above-mentioned slurry after polymerization was cooled to 25° C. and the aqueous monomer solution for the second stage was added to the system and then the system was held for 30 minutes under replacement with nitrogen. The flask was immersed again in a water bath at 70° C. and the temperature was raised to perform polymerization, so that a slurry after polymerization of the second stage was obtained.

Subsequently, the temperature was raised by using an oil bath at 125° C. and 284.8 g of water was removed to the outside of the system under reflux of n-heptane by azeotropically distilling water and n-heptane, and then 8.11 g (0.00186 mol) of a 4% by mass aqueous solution of ethylene glycol diglycidyl ether was added as a post-crosslinking agent. The resulting mixture was kept at 80° C. for 2 hours and then dried by removing n-heptane, so that 228.5 g of a water-absorbent resin was obtained. The results of property measurement are shown in Table 1.

Comparative Example 1

The same operations as those of Example 1 were carried out except that the amount of water to be removed during azeotropic distillation was changed to 260.2 g and the amount of the 2% by mass aqueous solution of ethylene glycol diglycidyl ether as a post-crosslinking agent was changed to 4.48 g (0.000514 mol) in Example 1, so that 231.2 g of a water-absorbent resin was obtained. The results of property measurement are shown in Table 1.

Comparative Example 2

The same operations as those of Example 1 were carried out except that the amounts of the ethylene glycol diglycidyl ether to be added to the aqueous monomer solutions for the first stage and the second stage were changed to 0.038 g (0.000218 mol) and 0.053 g (0.000304 mol), respectively, and the amount of water to be removed during azeotropic distillation was changed to 284.8 g in Example 1, so that 228.4 g of a water-absorbent resin was obtained. The results of property measurement are shown in Table 1.

Comparative Example 3

The same operations as those of Example 1 were carried out except that the amounts of the ethylene glycol diglycidyl ether to be added to the aqueous monomer solutions for the first stage and the second stage were changed to 0.008 g (0.0000459 mol) and 0.011 g (0.0000631 mol), respectively, the amount of the 2% by mass aqueous solution of ethylene glycol diglycidyl ether as a post-crosslinking agent was changed to 4.91 g (0.000563 mol), and the amount of water to be removed during azeotropic distillation was changed to 272.3 g in Example 1, so that 229.6 g of a water-absorbent resin was obtained. The results of property measurement are shown in Table 1.

Comparative Example 4

The same operations as those of Example 1 were carried out except that the amounts of the ethylene glycol diglycidyl ether to be added to the aqueous monomer solutions for the first stage and the second stage were changed to 0.002 g (0.0000114 mol) and 0.003 g (0.0000172 mol), respectively in Example 1, so that 228.7 g of a water-absorbent resin was obtained. The results of property measurement are shown in Table 1.

Comparative Example 5

The same operations as those of Example 1 were carried out except that the cooling temperature before adding the aqueous monomer solution for the second stage was changed to 26° C., the amount of water to be removed during azeotropic distillation was changed to 286.3 g and the amount of the 4% by mass aqueous solution of ethylene glycol diglycidyl ether as a post-crosslinking agent was changed to 11.76 g (0.00270 mol) in Example 1, so that 229.8 g of a water-absorbent resin was obtained. The results of property measurement are shown in Table 1.

Using the water-absorbent resin obtained in each of the Examples and the Comparative Examples, an absorbent material and an absorbent article were prepared and their liquid permeation rate, amount of re-wet of liquid, and shape retention property (deformation time) were evaluated by the method described below. The results are shown in Table 1.

<Performance of Absorbent Article>

(a) Preparation of Test Liquid

In a 10-L container was placed an appropriate amount of distilled water, and then 100 g of sodium chloride, 3.0 g of calcium chloride dihydrate, and 6.0 g of magnesium chloride hexahydrate were added and dissolved. Subsequently, 0.25 g of polyoxyethylene nonylphenyl ether was added, and then distilled water was further added, thereby adjusting the total mass to 10 kg. Moreover, the resulting mixture was colored with a small amount of Blue No. 1 to prepare a test solution.

(b) Production of Absorbent Article 10 g of a water-absorbent resin and 10 g of crushed pulp (Rayfloc produced by Rayonier) were uniformly mixed by an air sheet making technique to form a sheet-like absorbent material core having a size of 42 cm×12 cm. Next, an absorbent material was prepared by compressing the absorbent material core by the application of a load of 196 kPa for 30 seconds with a roll press to the entire of the core while vertically sandwiching the core between two pieces of tissue paper each having a basis weight of 16 g/m$^2$. Moreover, an air-through type porous liquid-permeable sheet made of polyethylene and having a basis weight of 22 g/m$^2$ was placed over the absorbent material and a liquid-impermeable sheet made of polyethylene and having the same size and basis weight was placed below the absorbent material, and then the absorbent material was sandwiched and pressed therebetween to form an absorbent article A. The absorbent article A was cut into a size of 30 cm×12 cm to form an absorbent article B.

The absorbent article A was used for evaluating the liquid permeation rate and the amount of re-wet of liquid, and the absorbent article B was used for evaluating the shape retention property (deformation time).

(c) Liquid Permeation Rate

An absorbent article A was placed on a horizontal platform. A measurement device was placed at the central portion of the absorbent article A, the measurement device having been provided with a liquid-injection cylinder having an internal diameter of 3 cm that was positioned at the center of a weight having a size of 10 cm×10 cm and weighing 2 kg. 50 mL of a test liquid was poured into the cylinder at once and then the time required for the test liquid to completely disappear from the cylinder was measured with a stopwatch to find a first permeation time (second). Subsequently, the cylinder was removed and then the absorbent article was stored as it was. At 30 minutes and 60 minutes after the start of the first injection of the test liquid, the same operations were carried out with that measurement device at the same position as the first time and thereby the permeation time (second) for the second and third times was measured. The total time of the first time through the third time was taken as a liquid permeation rate. The smaller the liquid permeation rate, it can be said that the article is more preferred as an absorbent article. For example, the liquid permeation rate is preferably 400 seconds or less, more preferably 350 seconds or less.

(d) Amount of Re-wet of Liquid

After 60 minutes had elapsed from the completion of measuring the liquid permeation rate, a piece of filter paper of 10 cm on each side whose mass had been measured in advance (Wd (g), approximately 50 g) was placed near the test liquid injection position on the absorbent article A, and a 5-kg weight having a bottom area of 10 cm×10 cm was placed on the filter paper. After application of load for 5 minutes, the mass (We (g)) of the filter paper was measured and the increase in mass was defined as the amount of re-wet of liquid (g). The smaller the amount of re-wet of liquid, it can be said that the article is more preferred as an absorbent article. For example, the amount of re-wet of liquid is preferably 12 g or less, more preferably 10 g or less.

Amount of re-wet of liquid (g)=$We-Wd$ (e) Shape Retention Property (Deformation Time)

Figure 2:
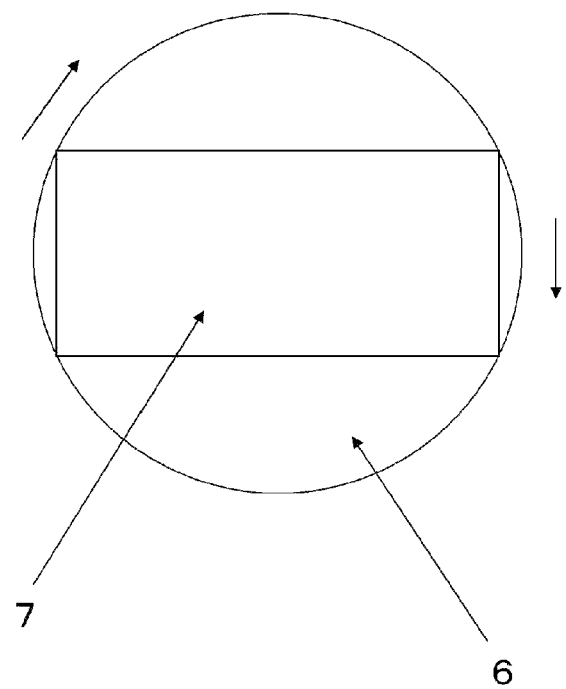
FIG. 2 is a top down view of a schematic arrangement in measuring the deformation time of an absorbent article.

A tubular cylinder having an internal diameter of 3 cm was placed near the center of the absorbent article B, and then 150 mL of a test liquid was poured into the cylinder at once and allowed to absorb. Five minutes after the pour of the test liquid, the absorbent article B was put on a cardboard being the same in size as the absorbent article B (basis weight: 3500 g/m$^2$), and the cardboard and the absorbent article B were fixed together with gummed tape and then put into a UNIPACK (produced by SEISANNIPPONSHA LTD., product No.: K-4). Subsequently, the absorbent article 7 put in the UNIPACK was set on a turntable 6 with a diameter of 30 cm set up so that a centrifugal force might be 30 G (425 rpm) as depicted in FIG. 2, and then deformation of the article caused by uneven distribution of the absorbent resin or crushed pulp in the absorbent material in the absorbent article B was visually checked every one minute, and the time when deformation was observed was taken as a deformation time. The measurement was carried out up to 40 minutes, and when no deformation of the absorbent material was observed, the deformation time was defined as being more than 40 minutes. The deformation time is an evaluation value that indicates the shape retention property of an absorbent material upon wetting and it is preferably 35 minutes or more, more preferably 40 minutes or more.

<Summary OF Evaluation Results>

As seen in Table 1, the water-absorbent resins obtained in Examples 1 to 5 exhibited excellent values with respect to water-retention capacity of physiological saline, water-absorption capacity of physiological saline under a load of 4.14 kPa, and tan δ of 50-fold swollen gel, and the absorbent articles obtained in the individual Examples were confirmed to be remarkably excellent in liquid permeation rate, amount of re-wet of liquid, and shape retention property (deformation time).

On the other hand, as to the water-absorbent resin obtained in Comparative Example 1, the water-absorption capacity of physiological saline under a load of 4.14 kPa of the water-absorbent resin was high, but the value of tan δ of a 50-fold swollen gel was low. Therefore, the amount of re-wet of liquid and so on of the absorbent article were excellent, but the deformation time was short and accordingly the shape retention property was poor. Comparative Example 2 was smaller than Comparative Example 1 in the value of tan δ of a 50-fold swollen gel and was shorter in deformation time. As to the water-absorbent resins obtained in Comparative Examples 3 and 4, since the 50-fold swollen gels of the water-absorbent resins were high in the value of tan δ, the deformation times of the absorbent articles were long and accordingly the articles were excellent in shape retention property, but the water-absorbent resins were low in water-absorption capacity of physiological saline under a load of 4.14 kPa, a gel blocking phenomenon occurred, and the absorbent articles exhibited lower liquid permeation rates. Especially in Comparative Example 4, the water-absorption capacity of physiological saline under a load of 4.14 kPa of the water-absorbent resin was low and the absorbent article had an increased amount of re-wet of liquid. In Comparative Example 5, the absorbent article had an increased amount of re-wet of liquid due to the low water-retention capacity of physiological saline of the water-absorbent resin.

The results described above have clearly shown that it is possible to improve an absorbent material and an absorbent article comprising a water-absorbent resin in all of liquid permeation rate, amount of re-wet of liquid, and shape retention property (deformation time) and make the absorbent material and the absorbent article have excellent performance by making the water-absorbent resin satisfy all of a water-retention capacity of physiological saline of 38 g/g or more, a water-absorption capacity of physiological saline under a load of 4.14 kPa of 15 mL/g or more, and a tan δ of a 50-fold swollen gel of $2.10 \times 10^{-2}$ or more.

TABLE 1

| | Water-absorption | | | | Absorbent article evaluation | | |
|---|---|---|---|---|---|---|---|
| | Water-retention capacity of physiological saline [g/g] | capacity of physiological saline under a load of 4.14 kPa [mL/g] | tanδ of 50-fold swollen gel [×10$^{-2}$] | Median particle size [μm] | Liquid permeation rate [second] | Amount of re-wet of liquid [g] | Shape retention property (Deformation time) [minute] |
| Example 1 | 40 | 22 | 2.40 | 345 | 330 | 10 | More than 40 |
| Example 2 | 40 | 25 | 2.32 | 350 | 320 | 9 | More than 40 |
| Example 3 | 41 | 23 | 2.23 | 380 | 321 | 7 | More than 40 |
| Example 4 | 42 | 21 | 2.15 | 430 | 315 | 9 | 40 |
| Example 5 | 47 | 21 | 2.28 | 360 | 340 | 8 | More than 40 |
| Comparative Example 1 | 39 | 27 | 2.02 | 370 | 353 | 10 | 15 |
| Comparative Example 2 | 40 | 15 | 1.66 | 370 | 380 | 12 | 1 |
| Comparative Example 3 | 46 | 14 | 2.20 | 350 | 405 | 13 | 40 |
| Comparative Example 4 | 45 | 7 | 2.86 | 390 | 540 | 18 | More than 40 |
| Comparative Example 5 | 36 | 24 | 2.22 | 360 | 410 | 15 | More than 40 |

DESCRIPTION OF REFERENCE SIGNS

X: measurement apparatus
1: burette section
10: burette
11: air inlet tube
12: cock
13: cock
14: rubber plug
2: lead tube
3: measuring platform
4: measuring section
40: cylinder
41: nylon mesh
42: weight
5: water-absorbent resin
6: turntable
7: absorbent article

The invention claimed is:

1. A method for producing a water-absorbent resin, wherein the water-absorbent resin has the following characteristics (1) to (3):
  (1) the water-retention capacity of physiological saline thereof is 38 g/g or more,
  (2) the water-absorption capacity of physiological saline under a load of 4.14 kPa thereof is 15 ml/g or more, and
  (3) the tan δ of a 50-fold swollen gel thereof is 2.10×10$^{-2}$ or more, and
wherein the method comprises a first step and a second step each defined below:
  the first step of performing reversed phase suspension polymerization of a water-soluble ethylenically unsaturated monomer in the presence of a radical polymerization initiator and an internal-crosslinking agent in a hydrocarbon dispersion medium, wherein an amount of the internal-crosslinking agent used is 0.000015 to 0.00020 mol per mol of the water-soluble ethylenically unsaturated monomer subjected to the polymerization; and
  the second step of crosslinking suspension polymerized particles obtained in the first step with a single addition of post-crosslinking agent, wherein an amount of the post-crosslinking agent used is 0.00025 to 0.0010 mol per mol of the water-soluble ethylenically unsaturated monomer subjected to the polymerization.

2. The method for producing a water-absorbent resin according to claim 1, wherein the water-soluble ethylenically unsaturated monomer is at least one selected from the group consisting of (meth)acrylic acid and salts thereof, (meth)acrylamide, and N,N-dimethylacrylamide.

3. The method for producing a water-absorbent resin according to claim 1, wherein the internal-crosslinking agent and the post-crosslinking agent are polyglycidyl compounds.

4. The method for producing a water-absorbent resin according to claim 1, wherein the amount of the internal-crosslinking agent to be used in the first step is 0.000030 to 0.000080 mol per mol of the water-soluble ethylenically unsaturated monomer subjected to the polymerization, and wherein the amount of the post-crosslinking agent used in the second step is 0.00044 to 0.00076 mol per mol of the watersoluble ethylenically unsaturated monomer subjected to the polymerization.

* * * * *